United States Patent [19]
Silverman

[11] Patent Number: 5,561,051
[45] Date of Patent: Oct. 1, 1996

[54] SCREEN FOR INHIBITORS OF CHITINASE

[75] Inventor: Sanford J. Silverman, Roosevelt, N.J.

[73] Assignee: American Cyanamid Company, Madison, N.J.

[21] Appl. No.: 259,409

[22] Filed: Jun. 14, 1994

[51] Int. Cl.$^6$ .............................. C12Q 1/34; C12N 9/30; C08B 37/08
[52] U.S. Cl. ................. 435/18; 435/4; 435/101; 435/195; 435/20.3; 435/223; 435/224; 435/256.1; 435/911; 435/942; 536/17.4; 536/20; 536/55.1; 536/55.2; 436/164; 436/172; 514/27; 514/53
[58] Field of Search ................... 435/18, 4, 101, 435/175, 195, 203, 223, 224, 256.1, 911, 942, 17.4; 536/20, 55.1, 55.2; 436/164, 172; 514/27, 53

[56] References Cited

PUBLICATIONS

Somers, P. J. B., et al., Method for the Detection and Quantitation of Chitinase Inhibitors in Fermentation Broths; Isolation and Insect Life Cycle Effect of A82516, The Journal of Antibiotics, vo. XL No. 12, pp. 1751–1756, (1987).
Ludwig et al, *FEMS Microbiology Letters*, vol. 69, pp. 61–66, 1990.
Milewski et al, *Journal of General Microbiology*, vol. 138, pp. 2545–2550, 1992.
Barrett–Bee et al, *Journal of General Microbiology*, vol. 130, pp. 1857–1861, 1984.
Cabib, *Methods in Enzymology*, vol. 161, (Bioruoss, Pt. B). pp. 424–426, 1988.
Nishimoto et al, *Biological Abstracts*, vol. 92, No. 10, Ref. #110946, 1992 (J. Antibiot, 44(7):716–722, 1991).
Leah et al, *The Journal of Biological Chemistry*, vol. 266, No. 3, pp. 1564–1573, Jan. 25, 1991.
Cabib et al, *Journal of General Microbiology*, vol. 138, pp. 97–102, 1992.
Tronsmo, Arne, et al., Detection and Quantification of N–Acetyl–$\beta$–D–glcosaminidase, Chitobiosidase, and Endo-chitinase in Solutions and on Gels, Analytical Biochemistry 208, 74–79 (1993).

*Primary Examiner*—Elizabeth C. Weimar
*Assistant Examiner*—Abdel A. Mohamed
*Attorney, Agent, or Firm*—Darryl L. Webster; James J. Harrington

[57] ABSTRACT

The present invention is directed to a method for screening samples for the identification of agents exhibiting potential fungicidal and insecticidal activity for a wide variety of agricultural, medical and pharmaceutical uses. The method utilizes cells that comprise a plasmid-born CTS gene of *Saccharomyces cerevisiae*, which allows for over expression of chitinase. Compounds that inhibit a hydrolyic action on methyl-umbelliferyltriacetyl chitotriose, but which are not toxic to the cells are detected by decrease in conversion of substrate

10 Claims, No Drawings

SCREEN FOR INHIBITORS OF CHITINASE

FIELD OF THE INVENTION

The present invention relates to a method of screening compounds that inhibit chitinase. More specifically, the present invention relates to the identification of antifungal, insecticidal and antiparasitic compounds for use in agricultural and pharmaceutical applications.

BACKGROUND OF THE INVENTION

The polysaccharide chitin is a structural cell wall component of most fungi and is the most abundant organic skeletal component of invertebrates, making up, for example, from about 25 to 60% of the dry weight of insect cuticles. Chitin consists primarily of linear polymers of the amino sugar N-acetyl-D-glucosamine joined in 1,4-β-glucosidic linkage. Thus, chitin bears a close resemblance to cellulose, the major structural polysaccharide of plants, the only chemical difference being that in chitin the hydroxyl group on the 2-position is an acetoamido group instead of an hydroxyl group. However, because of its widespread occurrence in fungi and arthropods, the total world-wide production of chitin vastly exceeds cellulose.

Many fungi and arthropods having chitinous cell walls or exoskeletons are injurious to plants and animals, causing a legion number of diseases including, but not limited to, wheat eyespot, rice sheath blight, damping off, apple scab, pepper botrytis, rice blast, sugar beet cercospora, tomato early blight, wheat leaf rust, and wheat powdery mildew. Fungal species also cause a myriad of cutaneous and systemic mycoses in human beings and other animals, including, but not limited to, candidiasis, histoplasmosis, blastomycosis, pneumocystis, sporotrichosis and cryptococcosis. Insects can act as vectors of viruses causing arboviral encephalitides, yellow fever, and dengue, protozoa causing malarias, trypanosomiases, and leishmaniases, and various harmful helminths. Crustaceans also carry some infectious helminths and trematodes.

Most fungicides and insecticides that are used to control or cure these diseases by killing or controlling their causative agents, intermediate hosts, or vectors employ various modes of action including physical poisons that suffocate or desiccate organisms; protoplasmic poisons such as arsenicals that kill by precipitating or deactivating proteins, enzymes or other cellular constituents; respiratory poisons that deactivate respiratory enzymes; and various poisons that affect different tissue systems such as tubules or nerves. Of course, preferred agents do not injure the host plant or animal, and most preferably have no effect whatsoever on the host. Because of the complexity and interdependence of life processes, however,, this goal is not always achieved, so that many fungicides and insecticides exhibit some toxicity to the host. Others cause unexpected side effects.

Since chitin is not a usual constituent of most plants and vertebrates, chitin biosynthesis inhibitors can be employed as selective antifungal and/or insecticide agents. Applied to ornamental or edible plants or animals, these offer the advantage of targeting undesirable fungi or insects without harming significantly the host plant or vertebrate animal. While much attention has been paid to chitin synthesis, there have been very limited studies targeting screens which exploit chitin degradation. 1-(2,6-Dichlorobenzoyl)-3-(3,4-dichlorophenyl) urea, for example, has been suggested as a chitin-inhibiting insecticide. Antifungals that have also been found to inhibit chitin synthesis include nikkomycin and polyoxin D.

SUMMARY OF THE INVENTION

It is an object of the present invention to provide a screening test for the identification of agents exhibiting potential fungicidal and insecticidal activity for a wide variety of agricultural, medical and pharmaceutical uses. This and other objects are accomplished by the present invention, which is directed to a method of screening compounds useful as antifungal, insecticidal and antiparasitic agents. The preferred method utilizes cells that comprise a plasmid-born CTS gene of *Saccharomyces cerevisiae* which allows for over expression of chitinase. Compounds that inhibit a hydrolytic action on methyl-umbelliferyltriacetyl chitotriose, but which are not toxic,to the cells, are detected by decrease in conversion of substrate. The present invention allows for the high volume screening of chemicals and fermentations for inhibitors of chitinase for insecticide, antiparasitic and fungicide applications.

DETAILED DESCRIPTION OF THE INVENTION

The discovery of most pharmaceutical and agricultural chemical products has resulted, at least in part, from the screening of either chemical libraries or natural products. A variety of screening systems that employ mammalian cells or yeast cells are well-known by those skilled in the art and have been described.

In the practice of this invention, test samples are incubated in the presence of cultures of any fungal species that produces chitin, such as unicellular fungi. A preferred method employs common baker's yeast, *Saccharomyces cerevisiae*, because it is readily available and easy to culture.

A preferred method comprises adding a test sample to a *Saccharomyces cerevisiae* culture. The test sample is introduced to a disk or a well on a culture plate in a standard diffusion assay using solidified media, or introduced into one of a series of equivalent tissue culture tubes or bottles in a standard turbidity assay using liquid media. The culture is incubated for such time under such conditions sufficient to observe yeast cell growth inhibition in a corresponding culture or culture plate area. The extent of growth of the culture containing or surrounding the test sample is compared with the extent of growth in the culture or culture area containing no test sample. The extent of toxicity of the test sample is determined by observing whether growth in the presences of test sample is substantially the same as growth in its absence.

The present invention relies on the expression of chitinase on the yeast cell surface and detection of enzyme activity with a substrate by observing the extent of substrate conversion.

Any type of substrate for chitinase that affords easy detection of enzyme activity can be employed including fluorescent substrates, colored dyes and turbid substrates that become clear when exposed to enzyme activity. Examples of substrates include: colloidal chitin, glycol chitin, 3–4 dinitrophenyl tetra-N-acetyl chitotetra oside, 4-methylumbelliferyl di-N-acetyl chitobioside, 4-methylumbelliferyl tri-N-acetyl chitotrioside, or 4-methylumbelliferyl tetra-N-acetyl chitotetraoside.

Any type of solidified or liquid media that will support growth and reproduction of *S. cerevisiae* may be employed as cultures in the method of this invention. Numerous yeast media are known to the skilled artisan, and include, for example, yeast synthetic dextrose (SD) containing glucose, vitamins, minerals, and water. Preferred media are solidified by adding agar or gelatin; especially preferred are media solidified with agar.

Growth in solidified cultures is ordinarily observed visually as turbid areas of growth around disks or wells in the culture plate. Growth in liquid cultures is observed visually, but is ordinarily determined spectrophotometrically as enhanced optical density (OD) at about 550 to 650 nm.

A distinct advantage of the invention is its speed and simplicity. Baker's yeast is readily available and inexpensive. Using solidified media in culture plates, the protocol is extremely simple. Many samples can be readily analyzed in a short time.

It is another advantage of the invention that only small amounts of biochemical or chemical agents are required in the test. In a standard assay, for example, which employs solidified media in a plate, as little as 20 μg of a biochemical or chemical test sample can be applied to a disk or in a well.

In a preferred embodiment of this invention, the screen relies on the expression of excess chitinase on the cell surface and direct detection of enzyme activity with a fluorescent substrate. This embodiment is achieved by using yeast cells transformed with a plasmid carrying the chitinase gene. The transformed yeast cells are dispersed and grown in agar, substrate is applied and the extent of the reaction is assayed by observation of the plate under ultraviolet illumination.

In a preferred embodiment of the invention, the fluorescent substrate is 4-methylumbelliferyl-tri-N-acetyl chitotrioxide (MUC).

In a preferred embodiment of the invention, the chitinase gene is carried on plasmid pCT21 which is essentially the same as plasmid pCT3 (Kuranda, M. J. and Robbins, P. W., (1987) Proc. Natl. Acad. Sci. USA vol. 84, 2585–2589) except that the vector sequences comprise the well known and commercially available YEp24 instead of the described YEAp24. pCT21 over-expressed chitinase from 4–25 fold over wild type cells lacking the plasmid.

In a particularly preferred embodiment, the present invention comprises a primary screen and secondary screen which increases both sensitivity and specificity of the invention. It should be understood by those skilled in the art that the present invention can be practiced using the primary screening alone, the secondary screen alone or a combination of the primary screen and secondary screen. One skilled in the art should also appreciate that the primary screen could be practiced after the secondary screen depending on the ultimate objective of the invention.

Standard in vitro and in vivo fungicide and insecticide discovery screens are employed as tertiary tests to prioritized actives from the present primary screen and the secondary screen. These in vitro screens test samples for their ability to inhibit the growth of selected phytopathogenic fungi cultured in nutrient agar (or insects). These include fungi causing wheat eyespot (*Pseudocercosporella herpotrichoides*), rice sheath blight (*Rhizoctonia solani*) and damping off (*Fusarium oxysporum*); all synthesize chitin-containing cell walls.

In in vivo screens, a variety of phytopathogenic fungi are used to infect plants treated with test compounds. Active compounds block or reduce the appearance of disease symptoms. A number of model plant infections are employed in the screen and include chitin-containing fungi that cause apple scab (*Venturia inaequalis*), pepper botrytis (Botrytis cincerea), rice blast (*Pyriculair oryzae*), sugar beet cercospora (*Cercospora beticola*), tomato early blight (*Alternaria solani*), wheat leaf rust (*Puccinia recondita tritici*), and wheat powdery mildew (*Erysiphe graminis tritici*). The most potent test compounds in these assays are active in the 10 ppm range.

The following examples are presented to further illustrate and explain the present invention and should not be taken as limiting in any regard.

EXAMPLES

Example 1

Preparation of Yeast Extracts (Chitinase extract)

Inoculate 200 ml and grow EC18-4B pCT as for primary screen. Centrifuge culture at 300 rpm for 10 min. Pour off supernatant, re-spin 1 min and remove remaining supernatant. Resuspend cells in 4×1 ml of buffer (25 mM Mes-0.1% digitonin-0.1% 2-mercaptoethanol, pH 6.3, for chitinase; 0.1M Na citrate, pH 5.0 for glucanase) in a screw cap centrifuge tube. Add approximately 0.5 mm glass beads to just below the meniscus and Vortex vigorously or put on a Mini-Bead-Beater for approximately 2 minutes. Remove liquid, wash beads with 0.5ml buffer, add wash to the rest of the extract. Centrifuge at 10,000 rpm for 2 minutes. Remove supernatant, measure its volume and add ½ volume glycerol and vortex gently. Store in aliquots at −80° C. (the extracts are then tested in the appropriate enzyme assay to ensure sufficient activity and linearity over time. 5 μl and 45 minutes is standard) at 30° C.

Example 2

Primary in Vitro Enzyme Assay

Grow the cell to stationary phase (overnight) in SD plus supplements without agar and without chloramphenicol. The Uracil requirement is supplied by the chitinase gene-containing plasmid pCT21. To retain the plasmid uracil must NOT be added. Cells can be stored for one week or more after suspending them in the agar medium and pouring the plate. For large scale, high capacity screening add sterile glycerol (15% final volume) to the fresh, stationary phase cultures and store at −80° C. in aliquots appropriate for test plate volume.

If using frozen cells, allow to thaw at room temperature and vortex. Add cells at 1:50 to SD plus supplements (with chloramphenicol when testing and natural products) that has been melted and cooled to about 50° C. Allow to solidify and apply compounds with a Clonemaster, or cut wells and add fermentations robotically. The positive control is allosamidin (1.25 μg).

Allow cells to grow 24 hours at 30° C.

Melt the assay overlay agar, cool to about 50° C., and add MUC. Mix well and apply to plate situated on a level surface for even distribution of soft agar. A large square plate that has 150 ml of agar requires 330 ml of overlay.

When plates have cooled, place them back at 30° C. and score after about two hours.

Alternatively, MUC can be added directly to the SD plus supplements at the same time cells are added. In this case, no assay overlay agar is necessary.

While wearing UV-protective glasses, place plates on a UV transilluminator (cover off, agar face down) and observe level of blue fluorescence around wells. Mark wells with decreased fluorescence (compare to allosamidin). In normal light, determine whether decrease in fluorescence is due to growth inhibition. Score a compound positive that decreases fluorescence but does not inhibit growth.

To mimic chitinase inhibition, various high-pH solutions (which are known to inhibit chitinase) are applied to filter discs and placed on the agar. Good fluorescence is obtained after overlaying substrate, and a zone of inhibition is seen only with the strongest alkali solutions tested (e.g. 10M NaOH). Other material designed to mimic fermentations and the potential interfering compounds therein (proteases [e.g. 10 mg/ml] Proteinase K, trypsin), buffering capacity) are found not to cause a false positive signal. Antimicrobial test agents are unnecessary in this screen since antifungals and other compounds that nonspecifically inhibit growth are scored as negative. Allosamidin, an analog of the natural substrate chitin, is known to inhibit *Bombyx mori* and Saccharomyces chitinase, but not plant chitinases (e.g. the enzyme from yam). Allosamidin is very clearly positive at about 1.25–2.5 µg per application. However, the more recently found compound, demethylallosamidin has been shown to be 100 fold more active than allosamidin and should be observable at 0.0125 µg per application (500 ng/ml). Applying the compound at a high concentration in DMSO on the agar surface as is done for other high-volume plate screens works as well as filter disk application. The best results for "welled" plates is to apply the compounds in 25 µl in the well. In a reconstruction experiment 10 randomly chosen fermentation broths are "spiked" with 5 µg allosamidin in 25 µl and applied to a primary screen plate. All 10 wells are clearly positive, whereas the same broths without allosamidin are negative.

The secondary assay is much more sensitive. Allosamidin inhibits chitinase to approximately the 50% level at 100 ng/ml final concentration in the assay. No inhibition of glucanase is detectable.

The screen is tested with thirty four standard test compounds exhibiting a variety of modes of action as well as with seventy six compounds that comprise a standard panel of antibiotics, as disclosed in Tables 1 and 2. All were negative, as are fermanation 44D048, aristeromycin, diflubenzuron (dimilin) and known chitin synthase inhibitors polyoxin and nikkomycin.

For chemical bank screening approximately 0.03% of compounds are judged positive in the primary screen. After processing over 20,000 chemicals, none have passed the secondary screen. For natural products the primary screen results in 0.9% active, but in over 15,000 assays only 2 (0.013%) have passed the secondary screen.

TABLE 1

Standard Fungicide Panel

| Compound | Target |
| --- | --- |
| Amphotericin B | plasma membrane (polyene) |
| Cerulenin | fatty acid biosynthesis |
| Haloprogin | respiration |
| ketoconazole | ergosterol biosynthesis (lanosterol 14a-demethylase) |
| miconazole | ergosterol biosynthesis (lanosterol 14a-demethylase) |
| diniconazole | ergosterol biosynthesis (lanosterol 14a-demethylase) |
| econazole | ergosterol biosynthesis (lanosterol 14a-demethylase) |
| fenarimole | ergosterol biosynthesis (sterol d14 reductase) |
| tridemorph | ergosterol biosynthesis (sterol d14 reductase) |
| tolnaftate | ergosterol biosynthesis (squalene monooxygenase) |
| U18666A | ergosterol biosynthesis (squalene cyclase) |
| cycloheximide | protein biosynthesis |
| polyoxin D | chitin biosynthesis (cell wall) |
| nikkomycin | chitin biosynthesis (cell wall) |
| nocodazole | microtubule |
| benomyl | microtubule |
| maneb | multi-target |
| metalaxyl | rRNA biosynthesis |
| vinclozolin | lipid peroxidation |
| kanamycin | mitochondria |
| tunicamycin | glycoprotein biosynthesis |
| carboxin | succinate dehydrogenase |
| cyanobutarate | microtubule (plant) |
| antimycin | respiration |
| glyphosate | herbicide (aromatic amino acid biosynthesis) |
| phosphinothricin | herbicide (glutamine biosynthesis) |
| aminotriazole | herbicide (histidine biosynthesis) |
| sulfometuron methyl | herbicide (branched chain amino acid biosynthesis) |
| pendimethalin | herbicide (microtubule) |

TABLE 2

Standard Antibiotic Panel

| | |
| --- | --- |
| pimaricin (tennecetin) | streptogramin ("type") |
| monazomycin | nystatin |
| aspartocin | bacitracin |
| clavicin | citrinin |
| avoparcin | isoquinocycline |
| neutramycin | A1531 |
| leucomycin | AO341a |
| angustmycin A & C | gliotoxin |
| gibberellic acid | puromycin |
| puromycin aminonucleoside | BM123a |
| etamycin | mocimycin |
| neomycin | viomycin |
| netropsin | lincomycin |
| picromycin | A9537 |
| AN272a | levomycin |
| AM374 | antiprozoin |
| BL580 zeta | actithiazic acid |
| hamycin | carbomycin |
| frenolicin | fusarinic acid |
| BL580a | tylosin |
| declomycin | tetrahydro spiramycin |
| usnic acid | geldanamycin |
| Z1220A | BM782a |
| BO2964 complex | chloramphenicol |
| A8363 | actinomycin |
| BM123a | AD97 |
| phenazine a | paromomycin |
| streptomycin | A4825 |
| BO2964 complex | nucleocidin |
| nonactin | valinomycin |
| C19004 complex | avilamycin |
| V214W | V214X |
| vancomycin | ristocetin |
| relomycin | CO8078a |
| blastocidinS | 4-dedimethylamino-4-methylamino-anhydrotetracycline |

Example 3

Secondary in vitro Enzyme Assay

Actives from the primary screen are put through the secondary assay which takes about 2 hours to perform for several dozen samples, including preparation and analysis. This consists of two different in vitro enzyme assays: glucanase and chitinase (the target). Broths that inhibit chitinase but not glucanase in these tests are judged positive. Those that display an absolute differential for these enzymes are first priority leads. Broths that show greater than twice the inhibition of chitinase versus glucanase should be followed up with secondary priority.

For each primary screen positive two enzyme assays are performed in microtiter dish wells. For each set of assays, make a Mix of buffer, Substrate and water, and add fermentation broth and enzyme:

Chitinase: Mix=1M Na citrate: ¼ MUC: water, 5:10:20
Per assay:

| Mix | 35 µl |
|---|---|
| broth or water (control) | 10 µl |
| Chitinase extract | 5 µl |

Incubate for 45 min at 30° C., then add 100 µl glycine-NaOH, mix.

Glucanase: Mix =1M Na citrate:MUG:water, 5:10:20
Per assay:

| Mix | 35 µl |
|---|---|
| broth or water (control) | 10 µl |
| Chitinase extract | 5 µl |

Incubate as for chitinase. Read both assays in a fluorimeter (350 nm excitation, 440 nm emission). Compare controls for each to broth effect on each. Broths that inhibit chitinase at least twice as much as they inhibit glucanase are judged positive.

What is claimed:

1. A method of screening test samples for inhibition of chitinase including a primary in vitro enzyme assay and a secondary in vitro enzyme assay, said primary assay comprising the steps of:
   (a) adding test sample to a chitinase producing yeast culture, said culture containing a substrate for chitinase;
   (b) incubating said test sample in said culture under conditions sufficient to detect inhibition of chitinase enzyme activity;
   (c) comparing the extent of substrate conversion in an area around the test sample with the extent of substrate conversion in the area void of said test sample;
   (d.1) observing cell growth of the culture;
   (d.2) determining the presence of chitinase inhibition by observing the extent of substrate conversion; and said secondary assay comprising the steps of:
   (e) adding a test sample that exhibits chitinase inhibition in said primary assay to at least two secondary enzyme assays, said secondary enzyme assays selected from the group consisting of a chitinase assay and at least one other control enzyme assays in which the assay detects for the activity of an enzyme other than chitinase
   (f) incubating said test sample in said secondary enzyme assays under conditions sufficient to detect inhibition of chitinase and inhibition of said control enzyme assay;
   (g) simultaneously comparing chitinase inhibition and control enzyme inhibition; and
   (h) determining whether the extent of chitinase inhibition is greater than the control enzyme inhibition.

2. The method of claim 1 wherein the enzyme activity is of chitinase detected with a fluorescent substrate.

3. The method of claim 1 wherein the enzyme activity of chitinase is detected with a colored dye substrate.

4. The method of claim 1 wherein the enzyme activity of chitinase is detected with a clearing of turbidity.

5. The method of claim 1 wherein the substrate is selected from the group of consistng of colloidal chitin, glycol chitin, 3–4 dinitrophenyl tetra-N-acetyl chitotetra oside, 4-methylumbelliferyl di-N-acetyl chitobioside, 4-methylumbelliferyl tri-N-acetyl chitotrioside, and 4-methylumbelliferyl tetra-N-acetyl chitotetraoside.

6. The method of claim 1 wherein the substrate is 4-methylumbelliferyl tri-N-acetyl chitotrioside, or 4-methylumbelliferyl tetra-N-acetyl chitotetraoside.

7. The method of claim 1 wherein known chitinase inhibitors are selected from the group consisting of allosamidin and demethylallosamidin are employed as positive controls for measuring chitinase inhibition.

8. The method of claim 1 wherein the control enzyme assay of step (e) is a glucanase assay.

9. The method of claim 1 wherein the yeast culture overproduces chitinase.

10. The method of claim 9 wherein the yeast culture comprises plasmid pCT21.

* * * * *